United States Patent
Chen et al.

(10) Patent No.: US 10,125,396 B2
(45) Date of Patent: Nov. 13, 2018

(54) AFFINITY MEDIATED AMPLIFICATION METHOD OF TELOMERIC C-SSDNA AND DETECTION KIT

(71) Applicant: ZHEJIANG JFK BIOLOGICAL TECHNOLOGY CO. LTD., Hangzhou (CN)

(72) Inventors: Ran Chen, Hangzhou (CN); Xiaozheng Jin, Hangzhou (CN)

(73) Assignee: Zhejiang JFK Biological Technology Co. Ltd., Hangzhou (CN)

( * ) Notice: Subject to any disclaimer, the term of this patent is extended or adjusted under 35 U.S.C. 154(b) by 297 days.

(21) Appl. No.: 14/961,150

(22) Filed: Dec. 7, 2015

(65) Prior Publication Data

US 2016/0168641 A1   Jun. 16, 2016

Related U.S. Application Data (63) Continuation of application No. PCT/CN2014/078542, filed on May 27, 2014.

(30) Foreign Application Priority Data

Jun. 7, 2013 (CN) .......................... 2013 1 0228178

(51) Int. Cl.
| | | |
|---|---|---|
| *C12Q 1/68* | (2018.01) | |
| *C07H 21/02* | (2006.01) | |
| *C12Q 1/6883* | (2018.01) | |
| *C12Q 1/686* | (2018.01) | |
| *C12P 19/34* | (2006.01) | |
| *C07K 16/00* | (2006.01) | |

(52) U.S. Cl.
CPC ............ *C12Q 1/6883* (2013.01); *C12P 19/34* (2013.01); *C12Q 1/686* (2013.01)

(58) Field of Classification Search
CPC .............. C12Q 1/686; C12Q 2525/131; C12Q 2565/537; C12Q 1/6883; C12P 19/34
See application file for complete search history.

(56) References Cited

FOREIGN PATENT DOCUMENTS

| | | |
|---|---|---|
| CN | 102639713 | 8/2012 |
| CN | 102864233 | 1/2013 |
| CN | 102876792 | 1/2013 |
| CN | 103333958 | 10/2013 |

OTHER PUBLICATIONS

Henson, J.D. et al., Nature Biotechnol., vol. 27, pp. 1181-1185 plus Online methods (2009).*
International Search Report, issued in the corresponding International PCT application No. PCT/CN2014/078542, dated Sep. 4, 2014, 7 pages.

* cited by examiner

*Primary Examiner* — Teresa E Strzelecka
(74) *Attorney, Agent, or Firm* — Hamre, Schumann, Mueller & Larson, P.C.

(57) ABSTRACT

Provided in the present invention are an affinity mediated amplification method of telomeric C-ssDNA with a template probe and a detection kit using this method for performing alternative lengthening detection of telomeres.

6 Claims, 1 Drawing Sheet

Specification includes a Sequence Listing.

AFFINITY MEDIATED AMPLIFICATION METHOD OF TELOMERIC C-SSDNA AND DETECTION KIT

TECHNICAL FIELD

The present application relates to an amplification method of probed-templates through binding of telomeric C-ssDNA (ABTC), and a kit for detecting alternative lengthening of telomeres (ALTs) by means of the present method.

BACKGROUND

Telomere is a structure formed of DNA repeat sequence (TTAGGG)$_n$ and some binding proteins at both ends of the eukaryotic chromosome. The telomere has the function of protecting the end of the chromosome from deterioration or from fusion, and it plays an important role in chromosomal location, replication, protection and in control of cell growth and survival, and is closely correlated with the cells apoptosis, transformation and immortalization. The telomere replication is accomplished by telomerase, a special reverse transcriptase, rather than by the typical DNA polymerase. In somatic cells of a normal person, as the expression of the telomerase is shut down, the telomere at the end of the chromosome is gradually shortened with cell division until the cell stops dividing or undergoes apoptosis. Therefore, a seriously shortened telomere is an indicator of cell aging. By virtue of the discovery about how chromosomes are protected by telomeres and telomerase, which reveals the mystery of human aging and suffering from serious diseases including cancer, Elizabeth Blackburn from the University of California (San Francisco, US), Carol Greider from Johns Hopkins University (US), and Jack Szostak from Harvard Medical School (US) and were awarded 2009 Nobel Prize in Physiology and Medicine.

The cancer cell has the property of indefinite division and proliferation, wherein the telomeric DNA is extended by reactivating the expression of the telomerase for most cases. However, the maintenance of the telomere length may also be realized through a telomerase-independent mechanism. In some cancer cells, the telomerase is still in an inhibitory state, wherein the telomeric DNA is extended through a "non-telomerase mechanism", that is, Alternative Lengthening of Telomeres (ALT). The clinical research indicates that, in general, about 85-90% of the cancer cells are telomerase positive, and about 10-15% of the cancer cells are ALT positive, which means that this two mechanisms are alternative and the cancer cell is in a state of either this or that. For some cancers, the ALT positive rate is higher, for example, the ALT positive rate is nearly 60% for osteogenic sarcomas, nearly 40% for gastric cancers, about 30% for soft tissue sarcomas and astrocytoma, and about 25% for primary brain cancers and glioblastomas. More importantly, the cancer patient with positive ALT often has worse prognosis compared with that with positive telomerase. Therefore, the detection of ALT has a potential of being a reference for monitoring the disease condition and prognosis, and disease treatment. Theoretically, all the cancers can be detected by the combination of ALT detection and telomerase detection.

At present, the method for detecting and analyzing ALT mainly includes the following:

1. Determination of whether the telomere length of a cell can be maintained in the absence of the telomerase activity while the cells are successively divided and proliferated. This determination typically requires the successive division and subculture of the cells for 20-30 passages, and multiple detections of the telomerase activity and the telomere length, thus it is obviously time consuming and labor intensive.

2. Detection of the heterozygosity and fluctuation of the telomere length, this process can be accomplished by Southern blotting or FISH. The telomere length varies considerably among the ALT+ cell populations, wherein some cells have quite long telomere, and some have quite short telomere. The clinical specimen generally comprises a mixture of cancer cells/tissues and normal cells/tissues, and the telomere lengths in these two types of population are significantly different from each other, which causes difficulty to the determination of the ALT+ cells. Such detection suffers from complex operations and low sensitivity, for which at least 1000 cells are required.

3. Detection of ALT-related PML nucleosome. Copolymerization of telomeric DNA with PML protein is detected by probe hybridization in combination with immunofluorescence/immunohistochemistry. The PML nucleosome obtained from this copolymerization is one of the characteristics of ALT cells. Such detection suffers from complex operations and low sensitivity, for which about 1000 cells are required.

4. Detection of recombinant telomeric DNA structure with ALT characteristic. The T-loop structure formed by the recombination of ALT is detected by 2-D electrophoresis technology, which requires about $1 \times 10^7$ cells; and the C-loop is assayed by using a highly progressive φ29 DNA polymerase with the circular telomeric TC-ssDNA having characteristic of ALT as a template to synthesize high molecular weight telomeric TG-ssDNA, and the result is assayed by pulse electrophoresis and probe hybridization. Such detection has a sensitivity up to 1000 cells or higher, but requires the use of radioactive isotope, which is not suitable for clinical generalization.

TC-ssDNA (Telomeric C-single stranded DNA) is a single stranded DNA formed of the CCCTAA unit complementary to the repeat TTAGGG of telomeric G, which generally exists as an extrachromosomal circular DNA, is a specific marker of the ALT+ cells, and it does not exist in normal cells or telomerase positive cancer cells. Therefore, the presence of the ALT+ cells can be determined by detecting whether TC-ssDNA is present. PCR amplification has a quite high sensitivity in nucleic acid detection, so PCR amplification of TC-ssDNA will be a highly sensitive method for detecting ALT+ cells. However, because TC-ssDNA contains repeat CCCTAA sequence, and an upstream and a downstream primer recognition site are necessary for a PCR process, accordingly the TC-ssDNA cannot be used directly as a template for PCR amplification. In the present invention, the template probe is amplified by PCR by binding TC-ssDNA to the anchor probe and inhibiting the cleavage to the template probe through competitive binding, and the result of PCR amplification indicates the presence of TC-ssDNA, thereby the rapid and simple detection of the ALT+ cells with high sensitivity can be achieved.

SUMMARY

An object of the present invention is to provide a method for amplification of probed-templates through binding of telomeric C-ssDNA (ABTC), and a kit for detecting alternative lengthening of telomere (ALT) by using the method.

The following technical solutions are employed in the present invention.

A method for amplifying probed-templates through binding of telomeric C-ssDNA (TC-ssDNA) (ABTC) is provided, which comprises the following steps:

An anchor probe T is fixed into a reaction tube to obtain an anchor PCR tube. The sequence of the anchor probe T is a repeat sequence of the G sequence, that is, $(TTAGGG)_n$, wherein n is an integer from 6 to 10, and it can be complementarily bound to TC-ssDNA to give a duplex, and the Tm value of this duplex is designated as Tmt. The anchor probe T may be fixed by a conventional method in the art, and the solid matrix for immobilizing the anchor probe T may be a plastic centrifuge tube, magnetic bead, gel particle or other solid matrix that adsorbs and binds nucleic acid.

Preferably, the anchor PCR tube fixed with the anchor probe T is prepared as follows: 50 μl of a TBST buffer containing 0.1 pmol biotinylated anchor probe T is added to a 0.2 ml thin-wall PCR tube coated with streptavidin and stood at 37° C. for 1 hr. The liquid in the tube is aspirated off, and 100 μl of TBST buffer is added, pipetted, and the liquid is aspirated off. The tube is repeatedly washed 3 times, and then the liquid is aspirated off. 100 μl of TE buffer is added and the liquid in the tube is then aspirated off, the tube is sealed and stored at −20° C. for later use.

(2) A template probe G is synthesized, in the middle part thereof is a repeat sequence of the G sequence, namely, $(TTAGGG)_{(n-1)}$ (wherein n is the same as described in Step (1), that is, the repeat sequence here contains one less repetitive than that in Step (1)); and both ends of this template probe G are the PCR primer sequences of telomerase. An enzyme cleavage site is located between the G sequence and the primer sequence at one end, and this end is marked as end A. The template probe G can be complementarily bound to TC-ssDNA to give a duplex, wherein the Tm value thereof is designated as Tmc.

(3) An inhibitory probe S is synthesized, which is complementary to the region of the enzyme cleavage site at the end A of the template probe G. The inhibitory probe S can be complementarily bound to TC-ssDNA to give a duplex, wherein the Tm value thereof is designated as Tms. Tmc is 5° C. lower than Tmt, and 20-25° C. higher than Tms.

(4) A double-stranded DNA sequence is formed by the template probe G and the inhibitory probe S, and this DNA sequence designated as dsGS. The inhibitory sequence S can be bound to the template probe G to give a duplex, and the duplex has a Tm value of 20° C. lower than that of the duplex formed by template probe G binding bound to TC-ssDNA. When the inhibitory sequence S is bound to the template probe G, a complete BamHI recognition site is formed, which can be cleaved by the BamHI enzyme.

(5) A lysis buffer is added to the sample to be tested, the mixture is repeatedly pipetted, transferred to a centrifuge tube, and placed on ice for 10 min, and centrifuged at 4° C. The supernatant is removed and used as the lysate supernatant. The lysis buffer is conventionally known in the art, which contains a surfactant (e.g. Triton X-100, SDS or the like), a buffer used for releasing DNA from a cell or tissue lysis.

The sample to be tested may be obtained from tissues or cells, or from clinical specimen such as sputum (luggies) or blood.

When the sample is obtained from sputum, the lysate supernatant may be prepared as follows: 1-5 ml of sputum and 5-10 ml of a pretreatment buffer are mixed and agitated at 37° C. for 10 min, and centrifuged for 10 min at 4° C. and 5000 rpm. The supernatant is discarded. The pellet is mixed with 200 μl of lysis buffer and repeatedly pipetted, transferred to a 1.5 ml centrifuge tube, placed at room temperature for 10 min, and centrifuged at 15000 rpm for 20 min. The supernatant is removed and used as the lysate supernatant. The pretreatment buffer has a composition of PBS+ 0.1% (w/vol) DTT.

When the sample is obtained from cells, the lysate supernatant may be prepared as follows: the cells are cultured in a 24-well plate, and then the culture media is aspirated off. 200 μl of lysis buffer is added, the mixture is repeatedly pipetted, transferred to a 1.5 ml centrifuge tube, placed at room temperature for 10 min, and centrifuged at 15000 rpm for 20 min. The supernatant is removed and used as the lysate supernatant.

When the test sample is obtained from a tissue, the lysate supernatant may be prepared as follows: about 0.1 $cm^3$ of a tissue mass is placed into a 1.5 ml centrifuge tube, 200 μl of lysis buffer is added, the tissue mass is smashed, repeatedly pipetted, transferred to a 1.5 ml centrifuge tube, placed at room temperature for 10 min, and centrifuged at 15000 rpm for 20 min, the obtained supernatant is removed and used as the lysate supernatant.

(6) The lysate supernatant and dsGS are added to the anchor PCR tube, and the hybridization is carried out by incubating for 10-30 min at a temperature that is 5° C. lower than Tmc, at this temperature, the TC-ssDNA is bound to the anchor probe T, meanwhile the dsGS is melted; because the TC-ssDNA is a long cyclic DNA, the template probe G is also bound to the TC-ssDNA, then it is incubated for 10-30 min at a temperature that is 10° C. lower than Tms for hybridization, at this temperature, the remaining template probe G unbound to the TC-ssDNA forms a double-stranded DNA with the inhibitory probe S.

(7) The liquid is aspirated off, and a PCR reaction solution containing a restriction endonuclease and PCR primers is added, the mixture is incubated for 5-15 min at 37° C. for enzymatic cleavage, then the PCR process is carried out. The obtained PCR product is subjected to fluorescent quantification or analysis by agarose gel electrophoresis. During the detection of ALT, a (blank) lysis buffer is used as a negative control, and it is subjected to the same treatment and analysis as Steps (5)-(7), a positive result is determined if the Ct value of the sample is less than that of the blank lysis buffer and the absolute value of the difference therebetween is greater than or equal to 1. The integrated enzymatic cleavage reaction can prevent not only the amplification of the template probe G that is not hybridized and bound to the telomeric extension sequence, but also the cross contamination caused by the spread of trace amount of PCR product aerosol, thus ensuring the specificity and success rate of the PCR reaction.

In the case of the cells containing TC-ssDNA, the end A of the template probe G bound to TC-ssDNA cannot be bound to the sequence S, so the intactness of the enzyme cleavage site is destroyed, and the enzymatic cleavage cannot be performed, and the PCR reaction is able to be performed. In the case of the cells containing no TC-ssDNA, the end A of the template probe G is bound to the sequence S, exists as dsGS, which contains complete enzyme cleavable site so it will be enzymatically cleaved prior to the performance of PCR reaction, thus actually the PCR reaction cannot be performed. Therefore, the occurrence of PCR amplification indicates that the cells contain TC-ssDNA, that is, ALT positive cell exists.

Preferably, the sequence of the anchor probe T is ((TTAGGG)₇), i.e.:

(SEQ ID NO: 1)
5'-TTAGGGTTAGGGTTAGGGTTAGGGTTAGGGTTAGGGTTAGGG-3'.

The sequence of the template probe G is:

(SEQ ID NO: 2)
5'-AAGAGCCGCGAGCGATCC<u>TTAGGGTTAGGGTTAGGGTTAGGGTTAGGG</u>
<u>TTAG*GGATCC*</u>GTCACCCTGGATGCTGTAGG-3', where the middle shadow part is 6 units of G sequence (TTAGGG)₆, both ends thereof are PCR primer recognition sites, and the highlighted italicized part of the sequence is a BamHI recognition site.

The sequence of the inhibitory probe S is:

(SEQ ID NO: 3)
5'-GTGAC*GGATCC*CTAACC-3'.

The PCR primer sequences are:

```
The upstream primer:
                            (SEQ ID NO: 4)
5'-CCGTCACCCTGGATGCTGTAGG-3';
and
                            (SEQ ID NO: 5)
The downstream primer:

5'-AAGAGCCGCGAGCGATCCTT-3'.
```

Preferably, the lysis buffer in Step (5) has the following composition: 1 mmol/L of EDTA-Na, 1% (v/v) Triton X-100, 150 mmol/L of NaCl, 10% (v/v) glycerol, 0.1 mg/ml fish sperm DNA (commercially available), and 10 mmol/L Tris-HCl (pH7.5) as a solvent.

Preferably, the PCR reaction solution (PCR buffer+dNTP+SYBR Green I+Taq enzyme+BamHI+PCR primers) in Step (7) has a composition of: 50 mmol/L KCl, 1.5 mmol/L MgCl₂, 0.2 mmol/L dNTP, 0.05% Tween 20, 0.4× SYBR Green I (0.4× means that the final concentration of each component in the reaction solution is 0.4 time of that of the 1× SYBR Green I; and the stock solution commercially available from the Microprobe Corp generally has a concentration of 10000×, and is diluted in the PCR buffer to have a final concentration of 0.4× by volume for use), 1 U/50 μl of Taq enzyme, 4 U/50 μl BamHI, 0.2 umol/L of PCR primers, and 10 mmol/L of Tris-HCl (pH 9.0) as the solvent.

The present invention is further directed to a kit for detecting ALT, which substantially comprises: an anchor PCR tube containing an anchor probe T fixed therein, a template probe G, an inhibitory probe S, PCR primers, a PCR reaction buffer, Taq enzyme and BamHI enzyme. In addition to the above main reagents, the kit may further comprise dNTP, SYBR Green I, or TaqMan probe, as desired by those skilled in the art.

The sequence of the anchor probe T is:

(SEQ ID NO: 1)
5'-TTAGGGTTAGGGTTAGGGTTAGGGTTAGGGTTAGGGTTAGGG-3'.

The sequence of the template probe G is:

(SEQ ID NO: 2)
5'-AAGAGCCGCGAGCGATCC<u>TTAGGGTTAGGGTTAGGGTTAGGGTTAGGG</u>
<u>TTAG*GGATCC*</u>GTCACCCTGGATGCTGTAGG-3'.

The sequences of the PCR primers are:

```
upstream primer:
                            (SEQ ID NO: 4)
5'-CCGTCACCCTGGATGCTGTAGG-3';
and downstream primer:
                            (SEQ ID NO: 5)
5'-AAGAGCCGCGAGCGATCCTT-3'.
```

The sequence of the inhibitory probe S is:

(SEQ ID NO: 3)
5'-GTGAC*GGATCC*CTAACC-3'.

The PCR primer sequences include:

```
an upstream primer:
                            (SEQ ID NO: 4)
5'-CCGTCACCCTGGATGCTGTAGG-3';
and
                            (SEQ ID NO: 5)
a downstream primer:

5'-AAGAGCCGCGAGCGATCCTT-3'.
```

The PCR reaction buffer has a composition of: 50 mmol/L KCl, 1.5 mmol/L MgCl₂, 0.05% Tween 20, and 10 mmol/L Tris-HCl (pH 9.0) as a solvent.

Preferably, the kit can further comprise a cell lysis buffer having a composition of: 1 mmol/L EDTA-Na, 1% Triton X-100, 150 mmol/L NaCl, 10% glycerol, 0.1 mg/ml fish sperm DNA, and 10 mmol/L Tris-HCl (pH 7.5) as a solvent.

The present invention mainly has the following advantages: the method and kit according to the present invention are simple and feasible in operation, have a high specificity and a markedly increased sensitivity in the detection of ALT, and are suitable for use in the detection of cells or tissues derived from various sources including clinical specimens derived from sputum.

BRIEF DESCRIPTION OF THE DRAWINGS

Step S1: the cells are lysed to release the TC-ssDNA, in which the lysis buffer is added with a template probe G (TPB) and an inhibitory probe S (CSC), and the region of TPB binding to CSC includes an enzyme cleavage site (restriction site, RS).

Step S2: incubation is performed at such high temperature (for example, 55° C. as shown in the FIGURE) that the TC-ssDNA binds to the anchor probe T and the template probe G at this temperature, and then the mixture is incubated at a low temperature (for example, 37° C. as shown in the FIGURE), so that the template probe G unbound to the TC-ssDNA is bound to the inhibitory probe S.

Step S3: after aspiration off, a RE/PCR system is added, and the obtained mixture is incubated at 37° C., during which the template probe G bound to the TC-ssDNA cannot be enzymatically cleaved and is kept intact; and the template probe G bound to the inhibitory probe S is enzymatically cleaved; and Step S4: the PCR reaction is carried out and the template probe G is amplified, the result indicates the presence of TC-ssDNA.

DETAILED DESCRIPTION

Figure 1:
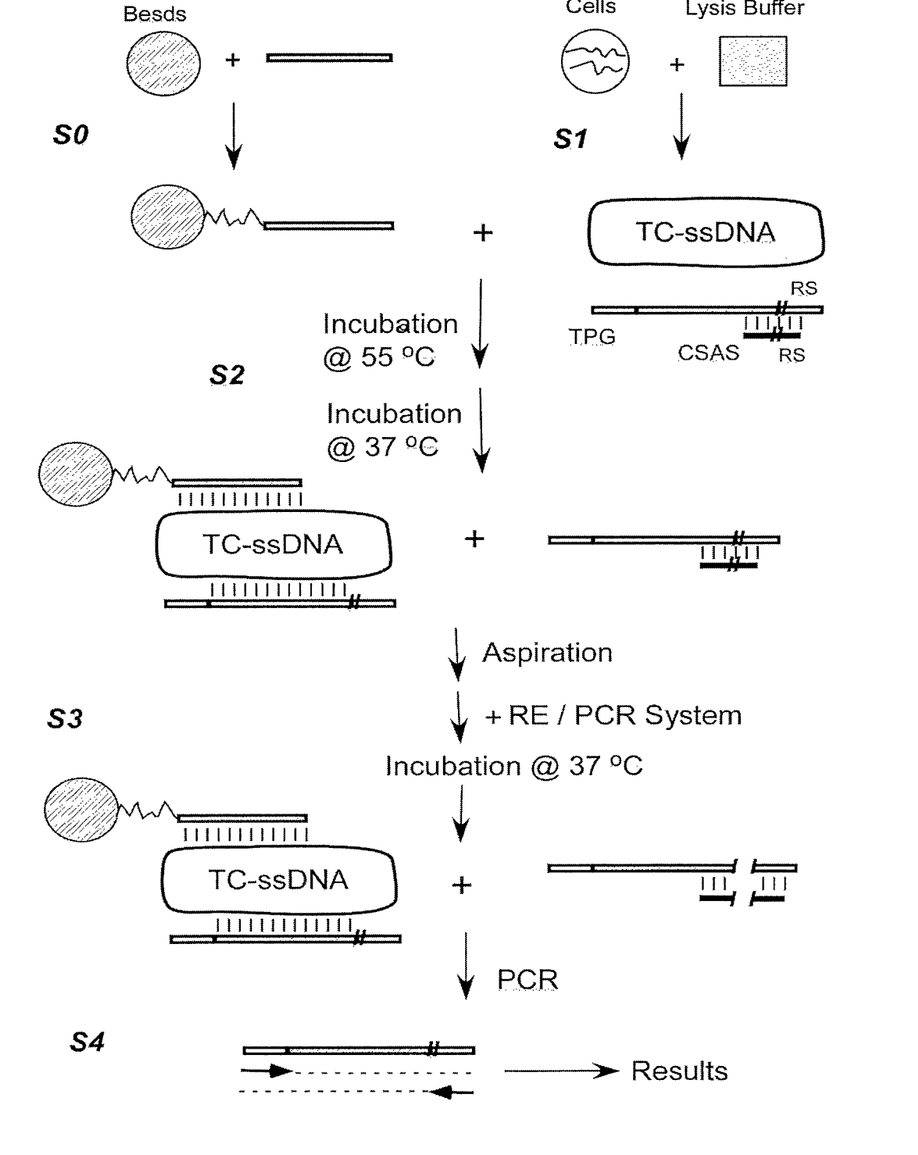
FIG. 1 is a schematic flow chart of a method according to the present invention, which includes Step S0: an anchor probe T (TS) is fixed to a solid matrix (e.g. beads)

The present invention will be described in further detail with reference to specific examples. However, the protection scope of the present invention is not limited thereto.

Example 1: Removal of the Interference with PCR from Trace Amount of dsGS by ABTC System Integrated with BamHI Enzyme The sequence of the anchor probe T is:

(SEQ ID NO: 1)
5'-TTAGGGTTAGGGTTAGGGTTAGGGTTAGGGTTAGGGTTAGGG-3'.

The sequence of the template probe G is:

(SEQ ID NO: 2)
5'-AAGAGCCGCGAGCGATCC*TTAGGGTTAGGGTTAGGGTTAGGGTTAGGG**TTAGGGGATCC*GTCACCCTGGATGCTGTAGG-3'.

The sequence of the inhibitory probe S is:

(SEQ ID NO: 3)
5'-GTGAC *GGATCC* CTAACC-3'.

The sequences of the PCR primers are:

```
upstream primer:
                                  (SEQ ID NO: 4)
5'-CCGTCACCCTGGATGCTGTAGG-3';
and downstream primer:
                                  (SEQ ID NO: 5)
5'-AAGAGCCGCGAGCGATCCTT-3'.
```

Preparation of anchor PCR tube: 50 μl of TBST buffer containing 0.1 pmol of biotinylated anchor probe T was charged into a 0.2 ml thin-wall PCR tube coated with streptavidin and stood at 37° C. for 1 hr. The liquid in the tube was aspirated off, and 100 μl of TBST buffer was added, the mixture was pipetted, and the liquid was aspirated off. The tube was repeatedly washed for 3 times, and then the liquid was aspirated off. 100 μl of TE buffer was added and the liquid in the tube was aspirated off. The tube was sealed and stored at −20° C. for later use.

The template probe G and the inhibitory probe S were dissolved in separated TE buffer respectively. 2 nmol/L of template probe G and 2 nmol/L inhibitory probe S were mixed, and incubated at 55° C. for 10 min and then at 37° C. for 10 min to obtain the dsGS with final concentration of 1 nmol/L, a part of which was taken and diluted to 0.01 nmol/L.

The PCR reaction solution (RE/PCR system) had a composition of: 50 mmol/L KCl, 1.5 mmol/L $MgCl_2$, 0.2 mmol/L dNTP, 0.05% (vol/vol) Tween20, 0.4× SYBR Green I, 1 U/50 μl Taq enzyme, 0.2 umol/L PCR primers, and 10 mmol/L Tris-HCl (pH 9.0) as a solvent.

16 reaction tubes were divided into 8 groups, each having 2 tubes. 20 μl of the above PCR reaction solution was added into each tube in each group. 2 μl of $ddH_2O$ was added to each tube of Groups 1-4, respectively, and 2 μl of 0.01 nmol/L dsGS was added to each tube of Groups 5-8, respectively. Then, 2 μl of 1 U BamHI in total was added to each tube of Groups 1 and 5 respectively, 2 μl of 2 U BamHI in total was added to each tube of Groups 2 and 6 respectively, 2 μl of 4 U BamHI in total was added to each tube of Groups 3 and 7 respectively, and 2 μl of $ddH_2O$ was added to each tube of Groups 4 and 8 respectively.

The reaction was carried out on a fluorescent PCR instrument with the following procedure: 37° C. for 10 min, 94° C. for 5 min, followed by 35 cycles of: 94° C. for 5 sec and 63° C. for 20 sec, and the amplification product was analyzed with SYBR green I fluorescent quantitative assay. The result is shown below.

| BamHI | Ct1-dsGS | Ct2-dsGS | Ct3-$ddH_2O$ | Ct4-$ddH_2O$ |
| --- | --- | --- | --- | --- |
| 1U | 22.48 | 22.35 | 30.52 | 30.76 |
| 2U | 25.61 | 25.74 | 30.44 | 30.21 |
| 4U | 30.46 | 30.28 | 30.39 | 30.60 |
| 0 | 17.96 | 17.79 | 30.75 | 30.47 |

It can be seen that the Ct value (resulted from the primer dimer) of the $ddH_2O$ control is greater than 30. In the absence of the BamHI enzyme, the Ct value of the dsGS tube is less than 18, which is far below the value of the control, suggesting that the template probe is amplified. After addition of the BamHI enzyme, the Ct value of the dsGS is obviously increased, suggesting that the intactness of the template probe is destroyed by the cleavage of dsGS by the BamHI enzyme, so that the number of template available to be amplified is declined. When the amount of BamHI is increased to 4 U, the Ct value of the dsGS tube is greater than 30, which is comparable with the value of the control, suggesting that the background arising from the amplification of the remaining small amount of dsTU can be effectively controlled by the RE/PCR system through cleavage.

Example 2: Removal of Interference Resulting from Contamination with Trace Amount of PCR Product by ABTC System Integrated with the BamHI Enzyme The primer and probe sequences, and the reaction tube were the same as those in Example 1. The amplification product was obtained from Group 8 in Example 1.

8 reaction tubes were divided into 4 groups, each group having 2 tubes. 20 μl of the PCR reaction solution (50 mmol/L KCl, 1.5 mmol/L $MgCl_2$, 0.2 mmol/L dNTP, 0.05% (vol/vol) Tween 20, 0.4× SYBR Green I, 1 U/50 μl Taq enzyme, 0.2 umol/L PCR primers, and 10 mmol/L Tris-HCl (pH 9.0) as the solvent) was added into each tube of each group. 2 μl $ddH_2O$ was added to each tube of Groups 1 and 2 respectively, and 2 μl of the amplification product at a dilution of $10^{-7}$ was added to each tube of Groups 3 and 4 respectively. Then, 2 μl of 4 U BamHI in total was added to each tube of Groups 1 and 3 respectively, and 2 μl of $ddH_2O$ was added to each tube of Groups 2 and 4 respectively.

The reaction was carried out on a fluorescent PCR instrument with the following procedure: 37° C. for 10 min, and 94° C. for 5 min, followed by 35 cycles: of 94° C. for 5 sec and 63° C. for 20 sec, and the amplification product was analyzed by SYBR green I fluorescent quantitative assay. The result is shown below.

| BamHI | Ct-Product | Ct-ddH$_2$O |
|---|---|---|
| 4 | 30.25 | 30.68 |
| 0 | 16.34 | 30.73 |

It can be seen that the Ct value (resulted from the primer dimer) of the ddH$_2$O control is greater than 30. With respect to the conventional PCR, when no BamHI is added to the system, the Ct value of the amplification product tube is less than 17, which is far below the value of the control, suggesting that the amplification product at a dilution of $10^{-7}$ can cause contamination to the conventional PCR reaction system, resulting in serious false positive results. After addition of 4 U BamHI enzyme, the Ct value of the amplification product tube is greater than 30, which is comparable with the value of the control, suggesting that the false positive results arising from the contamination with the trace amount of amplification product can be effectively controlled by the RE/PCR reaction system integrated with BamHI through cleavage.

Example 3: Detection of Human Lung Cancer SK-LU-1 Cells by the ABTC Method

The primer and probe sequences, the reaction tube, the lysis buffer and the RE/PCR system were the same as those in Example 1. SK-LU-1 was known ALT+ cells and commercially available from ATCC.

The detection method was as follows:

The SK-LU-1 cells were cultured in a 24-well plate (at a density of about 10-10000 cells/well), the media was aspirated off. 200 μl of a lysis buffer B (containing 0.1 nmol/L dsGS) was added into each well, the mixture was repeatedly pipetted, transferred to a 1.5 ml centrifuge tube, agitated at room temperature for 10 min, and centrifuged at 15000 rpm for 20 min. The supernatant was removed and used as the lysate supernatant.

The lysis buffer B had a composition of: 0.1 nmol/L dsGS, 1 mmol/L EDTA-Na, 1% (v/v) Triton X-100, 150 mmol/L NaCl, 10% (v/v) glycerol, 0.1 mg/ml fish sperm DNA (Sigma), and 10 mmol/L Tris-HCl (pH 7.5) as the solvent.

2) 50 μL of the lysate supernatant was added to a reaction tube, and incubated at 60° C. for 30 min and then at 37° C. for 10 min.

3) After aspiration off of liquid, 50 μl of the RE/PCR reaction system (containing 50 mmol/L KCl, 1.5 mmol/L MgCl$_2$, 0.2 mmol/L dNTP, 0.05% Tween 20, 0.4× SYBR Green I, 1 U/50 μl Taq enzyme, 4 U/50 μl BamHI, 0.2 umol/L PCR primers, and 10 mmol/L Tris-HCl (pH 9.0) as the solvent). The amplification was carried out on a PCR instrument with the following procedure; 37° C. for 10 min and 94° C. for 3 min, followed by 35 cycles of: 94° C. for 5 sec and 63° C. for 30 sec, and the amplification product was analyzed by SYBR green I fluorescent quantitative assay.

4) The operations in Steps 2)-3) were repeated with the lysis buffer B (containing 0.1 nmol/L dsGS).

5) When the Ct value≤29.50, the result was determined to be positive, and when the Ct value>29.50, the result was determined to be negative.

The result is shown below.

| Sample | Ct | Results |
|---|---|---|
| 10 cells | 29.37 | Positive |
| 100 cells | 25.82 | Positive |
| 1000 cells | 22.39 | Positive |
| 10000 cells | 18.94 | Positive |
| Lysis buffer | 30.15 | Negative |

It can be seen that the ALT positive result can be detected in 10-10000 SK-LU-1 cells by the ABTC method.

Example 4: Stability of Reaction Tubes Fixed with the Anchor Probe T Prepared in Large Quantity The reaction tube prepared above was packaged in a plastic bag, and stored at −20° C.

The primer and probe sequences, the lysis buffer B, and the RE/PCR system were the same as those in Example 3.

24 reaction tubes were divided into 6 groups, each having 4 tubes. After sealing, the tubes were stored at 37° C. for 1, 2, 3, 4, 5, and 6 days, and recorded as Groups 1, 2, 3, 4, 5, and 6.

1 ml of the lysate supernatant (containing 0.1 nmol/L dsGS) of 5×1000 SK-LU-1 cells was prepared following the method in Example 3 and used as a positive control; and the lysis buffer B (containing 0.1 nmol/L dsGS) was used as a negative control.

The operations were as described in Steps 2) and 3) of Example 3, and each group of reaction tubes had 2 positive controls and 2 negative controls.

When the Ct value was ≤29.50, the result was determined to be positive, and when the Ct value was >29.50, the result was determined to be negative.

The result is shown below.

| Group | Ct-Positive control 1 | Ct-Positive control 2 | Ct-Negative control 1 | Ct-Negative control 2 |
|---|---|---|---|---|
| 1 | 22.63 | 22.49 | 30.25 | 30.36 |
| 2 | 22.41 | 22.58 | 30.47 | 30.30 |
| 3 | 22.52 | 22.37 | 30.54 | 30.38 |
| 4 | 22.68 | 22.73 | 30.42 | 30.65 |
| 5 | 24.93 | 26.48 | 30.66 | 30.31 |
| 6 | 29.85 | 29.66 | 29.89 | 30.11 |

It can be seen that after storage at 37° C. for 1-4 days, the reaction tubes fixed with the anchor probe T prepared in large quantity have no influence on the detection results of ALT, but have a serious influence on the detection results after storage at 37° C. for 5 or more days.

Example 5: Detection of ALT in Human Osteogenic Sarcoma Cell Line U-2 OS by the ABTC Method The primer and probe sequences, the reaction tube, the lysis buffer, the reaction solution, and the RE/PCR system were the same as those in Example 3.

The detection method was as follows:

The U-2 OS cells (commercially available from ATCC) were cultured in a 24-well plate (at a density of about 10-10000 cells/well), the media was aspirated off. 200 μl of a lysis buffer (containing 0.1 nmol/L dsGS) was added into each well, the mixture was repeatedly pipetted, transferred to a 1.5 ml centrifuge tube, placed on ice for 20 min, and centrifuged at 15000 rpm for 20 min. The supernatant was removed and used as the lysate supernatant. The following operations were the same as those in Example 3. When the Ct value was ≤29.50, the result was determined to be positive, and when the Ct value was >29.50, the result was determined to be negative.

The result is shown below.

| Sample | Ct | Results |
|---|---|---|
| 10 cells | 28.96 | Positive |
| 100 cells | 25.64 | Positive |
| 1000 cells | 22.37 | Positive |
| 10000 cells | 19.08 | Positive |
| Lysis buffer | 29.53 | Negative |

It can be seen that the ALT positive result can be detected in 10-10000 U-2 OS cells by the ABTC method.

Example 6: ABTC Detection Kit for ALT

A kit of 8 Tests had a composition as shown below.

| Component | Function | Packing specification |
|---|---|---|
| 1) Concentrated pretreatment buffer | Pretreatment of the sample, and collection, enrichment, and washing of the cells 50-fold diluted with ddH$_2$O before use | 1 × 1.7 ml |
| 2) Lysis buffer | Lysis of cells, and negative control Direct use | 1 × 1.7 ml |
| 3) RE/PCR reaction solution | Enzymatic cleavage and PCR proliferation Direct use | 1 × 0.45 ml |
| 4) Positive control | Lysate supernatant of 1000 freshly frozen SK-LU-1 cells Direct use | 1 × 0.12 ml |
| 5) reaction tube | Fixed with telomerase primer Direct use | 1 × 8 |
| 6) Membrane seal | Sealing the reaction tube Direct use | 1 |
| 7) Instruction | Operation instructions and notices | 1 |

The concentrated pretreatment buffer had a composition of: 50×PBS+50 g/L DTT, and contained 1×PBS+1 g/L DTT after 50-fold dilution. The composition of 1×PBS was: NaCl 137 mM, KCl 2.7 mM, Na$_2$HPO$_4$ 10 mM, KH$_2$PO$_4$ 1.8 mM, and distilled water was used as the solvent.

The primer sequence, the lysis buffer, the reaction tube, and the RE/PCR reaction solution were the same as those in Example 3.

The operation steps were as follows:

The kit was removed from a frozen storage environment, thawed at room temperature, and temporarily stored at 4° C.

The concentrated pretreatment buffer was 50-fold diluted with 83 ml ddH$_2$O, to give a pretreatment buffer that was temporarily stored at 4° C.

A sample was collected, which might be cultured cells and tissues, or sputum, whole blood (supplemented with an anticoagulant), and urine.

The amount of the sample was recommended to be about 10-10$^6$ cultured cells, about 0.1 cm$^3$ tissue mass, about 2 ml of sputum, about 0.5 ml of whole blood, and about 10 ml of urine.

The sample was pretreated as follows: The cells cultured in suspension were collected by centrifugation, and then re-suspended in 10 ml of the pretreatment buffer. The tissue mass was soaked in 10 ml of the pretreatment buffer, and chopped. The sputum was agitated with 10 ml of the pretreatment buffer at 37° C. for about 10 min until the sputum was completely dissolved. 10 ml of the pretreatment buffer was directly added to the whole blood. After centrifugation of the urine, the pellet was re-suspended in 10 ml of the pretreatment buffer. The materials obtained above were all further centrifuged, the supernatant was discarded, and the pellet was carried on next step.

4) The lysis buffer was added to the pellet in an amount of 200 µl/sample, the mixture was repeatedly pipetted, transferred to a 1.5 ml centrifuge tube, placed at room temperature for 10 min, and centrifuged at 15000 rpm for 20 min.

5) 50 µl of the lysate supernatant was added to the reaction tube, and incubated at 60° C. for 30 min and then at 37° C. for 10 min.

6) The liquid was aspirated off, and then 50 µl of the RE/PCR reaction system (containing the PCR buffer, 0.2 µmol/L PCR primers, 0.2 mmol/L dNTP, 1 U Taq enzyme, and 4 U BamHI) was added. The amplification was carried out on a PCR instrument with the following procedure: 37° C. for 10 min and then 94° C. for 3 min, followed by 35 cycles of: 94° C. for 5 sec and 63° C. for 30 sec, and the amplification product was analyzed by SYBR green I fluorescent quantitative assay.

7) A negative control and a positive control were set in place of the lysate supernatant, and used in Steps 5)-6).

8) When the Ct value was ≤29.50, the result was determined to be positive, and when the Ct value was >29.50, a negative result was determined.

Example 6: Detection of ALT in Immortalized Human Fibroblast Cell Line SUSM-1 with the ABTC Detection Kit for ALT The cells (commercially available from ATCC) were subcultured in laboratory. The SUSM-1 cells were cultured in a 24-well plate (at a density of about 1-10$^6$ cells/well). The kit and operation steps were as described in Example 5. The lysis buffer was used as a negative control and the lysate supernatant of 1000 SK-LU-1 cells was used as a positive control.

When the Ct value was ≤29.50, a positive result was determined, and when the Ct value was >29.50, a negative result was determined. The result is shown below.

| Sample/Control | Ct | Results |
|---|---|---|
| 1 cell | 29.24 | Positive |
| 10 cells | 27.11 | Positive |
| 100 cells | 23.52 | Positive |
| 10$^3$ cells | 19.34 | Positive |
| 10$^4$ cells | 16.15 | Positive |
| 10$^5$ cells | 15.98 | Positive |
| 10$^6$ cells | 15.66 | Positive |
| Negative control | 30.79 | Negative |
| Positive control | 22.38 | Positive |

It can be seen that the ALT positive result can be detected in 1-10$^6$ SUSM-1 cells with the ABTC kit. However, when the cell number in the sample reaches to or exceeds 10$^4$, the Ct value does not decline obviously, suggesting that the amplification limiting factor varies from TC-ssDNA to the template probe, that is, the template probe is completely adsorbed and bound. Therefore, the number of the PCR template is not increased any more with increasing TC-ssDNA in the cells.

Example 7: Detection of ALT in Human Osteogenic Sarcoma Cell Line G-292 with the ABTC Detection Kit for ALT The cells (commercially available from ATCC) were subcultured in laboratory. The G-292 cells were cultured in a 24-well plate (at a density of about $10$-$10^5$ cells/well). The kit and operation steps were as described in Example 5.

When the Ct value was ≤29.50, a positive result was determined, and when the Ct value was >29.50, a negative result was determined. The results are shown below.

| Sample/Control | Ct | Results |
|---|---|---|
| 10 cells | 27.79 | Positive |
| 100 cells | 24.25 | Positive |
| $10^3$ cells | 19.67 | Positive |
| $10^4$ cells | 16.20 | Positive |
| $10^5$ cells | 15.93 | Positive |
| Negative control | 30.13 | Negative |
| Positive control | 22.63 | Positive |

It can be seen that the ALT positive result can be detected in $10$-$10^5$ G-292 cells with the ABTC kit, and in this range, the higher the cell number is, the lower the Ct value is, suggesting that the ABTC detection for ALT is of great value in quantitative detection.

Example 8: Detection of ALT in Human Osteogenic Sarcoma Cell Line SAOS-2 with the ABTC Detection Kit for ALT The cells (commercially available from ATCC) were subcultured in laboratory. The SAOS-2 cells were cultured in a 24-well plate (at a density of about $10$-$10^5$ cells/well). The kit and operation steps were as described in Example 5. When the Ct value was ≤29.50, a positive result was determined, and when the Ct value was >29.50, a negative result was determined.
i. The result is shown below.

| Sample/Control | Ct | Results |
|---|---|---|
| 10 cells | 26.73 | Positive |
| 100 cells | 23.35 | Positive |
| $10^3$ cells | 20.09 | Positive |
| $10^4$ cells | 16.68 | Positive |
| $10^5$ cells | 15.79 | Positive |
| Negative control | 30.42 | Negative |
| Positive control | 22.53 | Positive |

It can be seen that the ALT positive result can be detected in $10$-$10^5$ SAOS-2 cells with the ABTC kit, and in this range, the higher the cell number is, the lower the Ct value is, suggesting that the ABTC detection for ALT is of great value in quantitative detection.

Example 9: Detection of ALT in Sputum Specimen from Lung Cancer Patient with the ABTC Detection Kit for ALT 20 lung cancer patients were in stage I as diagnosed by needle biopsy of tissues, and had not received an operation. The sputum was freshly collected in the morning.

The kit and operation steps were as described in Example 5.

When the Ct value was ≤29.50, a positive result was determined, and when the Ct value was >29.50, a negative result was determined.

Among the 20 lung cancer patients, 3 were detected to be ALT positive, and 17 were ALT negative. 2 normal person (who had sputum due to smoking, and were healthy by recently physical examination) control were detected to be ALT negative.

| Sample/Control | Ct | Results |
|---|---|---|
| Negative control | 30.52 | Negative |
| Positive control | 22.69 | Positive |
| Lung cancer patient JFK-ZJL-201 | 29.76 | Negative |
| Lung cancer patient JFK-ZJL-202 | 30.29 | Negative |
| Lung cancer patient JFK-ZJL-203 | 30.73 | Negative |
| Lung cancer patient JFK-ZJL-204 | 30.44 | Negative |
| Lung cancer patient JFK-ZJL-205 | 21.81 | Positive |
| Lung cancer patient JFK-ZJL-206 | 29.55 | Negative |
| Lung cancer patient JFK-ZJL-207 | 31.38 | Negative |
| Lung cancer patient JFK-ZJL-208 | 30.20 | Negative |
| Lung cancer patient JFK-ZJL-209 | 29.95 | Negative |
| Lung cancer patient JFK-ZJL-210 | 30.57 | Negative |
| Lung cancer patient JFK-ZJL-211 | 31.22 | Negative |
| Lung cancer patient JFK-ZJL-212 | 29.88 | Negative |
| Lung cancer patient JFK-ZJL-213 | 30.74 | Negative |
| Lung cancer patient JFK-ZJL-214 | 20.54 | Positive |
| Lung cancer patient JFK-ZJL-215 | 30.86 | Negative |
| Lung cancer patient JFK-ZJL-216 | 30.19 | Negative |
| Lung cancer patient JFK-ZJL-217 | 24.41 | Positive |
| Lung cancer patient JFK-ZJL-218 | 30.97 | Negative |
| Lung cancer patient JFK-ZJL-219 | 29.78 | Negative |
| Lung cancer patient JFK-ZJL-220 | 30.66 | Negative |
| Normal individual JFK-ZJN-001 | 30.49 | Negative |
| Normal individual JFK-ZJN-002 | 30.68 | Negative |

It can be seen that the ALT positive result can be detected in fresh sputum from some lung cancer patients with the ABTC detection kit.

Example 10: Detection of ALT in Surgically Removed Gastric Cancer Tissues with the ABTC Detection Kit for ALT The surgically removed tissues from 12 gastric cancer patients were frozen at −80° C. About 30 mg of frozen gastric cancer tissue was clipped by sterilized ophthalmic scissors. 10 ml of the pretreatment buffer was added, and centrifuged. The supernatant was discarded. 200 μl of the lysis buffer was added, and agitated at room temperature for 10 min. The following operations were carried out as described in Example 5. The kit was the same as Example 5. When the Ct value was ≤29.50, a positive result was determined, and when the Ct value was >29.50, a negative result was determined.

The tissues from 5 gastric cancer patients were detected to be ALT positive, and the tissues from 7 gastric cancer patients were detected to be ALT negative.

| Sample/Control | Ct | Result |
| --- | --- | --- |
| Negative control | 30.62 | Negative |
| Positive control | 22.45 | Positive |
| Gastric cancer patient JFK-ZJG-001 | 30.24 | Negative |
| Gastric cancer patient JFK-ZJG-002 | 29.78 | Negative |
| Gastric cancer patient JFK-ZJG-003 | 20.55 | Positive |
| Gastric cancer patient JFK-ZJG-004 | 21.37 | Positive |
| Gastric cancer patient JFK-ZJG-005 | 24.87 | Negative |
| Gastric cancer patient JFK-ZJG-006 | 30.14 | Negative |
| Gastric cancer patient JFK-ZJG-007 | 29.71 | Negative |
| Gastric cancer patient JFK-ZJG-008 | 30.77 | Negative |
| Gastric cancer patient JFK-ZJG-009 | 25.34 | Positive |
| Gastric cancer patient JFK-ZJG-010 | 27.17 | Positive |
| Gastric cancer patient JFK-ZJG-011 | 29.62 | Negative |
| Gastric cancer patient JFK-ZJG-012 | 27.48 | Positive |

It can be seen that the ALT positive result can be detected in surgically removed frozen cancer tissues from some gastric cancer patients with the ABTC detection kit.

Example 11: Detection of ALT in Human Lung Cancer Cell Line A549 with the ABTC Detection Kit for ALT The cells (commercially available from ATCC) were subcultured in laboratory. The A549 cells were known telomerase positive and ALT negative cells, which were cultured in a 24-well plate (at a density of about 10-10$^5$ cells/well). The kit and operation steps were the same as Example 5. When the Ct value was ≤29.50, a positive result was determined, and when the Ct value was >29.50, a negative result was determined. The result is shown below.

| Sample/Control | Ct | Result |
| --- | --- | --- |
| 10 cells | 30.23 | Negative |
| 100 cells | 30.65 | Negative |
| 10$^3$ cells | 30.42 | Negative |
| 10$^4$ cells | 30.57 | Negative |
| 10$^5$ cells | 30.28 | Negative |
| Negative control | 30.76 | Negative |
| Positive control | 22.65 | Positive |

It can be seen that the 10-10$^5$ A549 cells are all ALT negative as detected by ABTC, further confirming the specificity of the ABTC method for detecting ALT.

Example 12: Replacing TaqMan Probe with SYBR Green I had No Influence on Detection of ALT by the ABTC Method The primer and probe sequence, the reaction tube, the lysis buffer, and the RE/PCR system were the same as those in Example 3. In the RE/PCR system, the SYBR green I was replaced by 0.5 μmol/L TaqMan probe (having a sequence of 5'-CCTAACCCTAACCCTAACCCTAACCCTAACCCTA-3' (SEQ ID NO: 6) with 5' end and 3' end being labeled with FAM and TAMRA, respectively). The cells were SK-LU-1 cells. The detection method was the same as Example 5. The FAM fluorescent quantitative assay was used in place of the SYBR green I assay. When the Ct value was ≤30, a positive result was determined, and when the Ct value was >30 or no Ct value is obtained, a negative result was determined.

The result is shown below.

| Sample | Ct | Result |
| --- | --- | --- |
| Lysis buffer | No Ct | Negative |
| 10 cells | 29.36 | Positive |
| 100 cells | 25.72 | Positive |
| 1000 cells | 22.43 | Positive |
| 10000 cells | 19.01 | Positive |

It can be seen that the ALT positive result can be detected in 10-10000 SK-LU-1 cells by the ABTC method using TaqMan probe.

What is claimed is:

1. A method for amplification of probed-templates through binding of telomeric C-ssDNA comprising:
   (1) immobilizing an anchor probe T into a reaction tube to obtain an anchor PCR tube, the anchor probe T having a sequence of $(TTAGGG)_n$, where n is an integer selected from 6 to 10, and the anchor probe T has an ability to complementarily bind to the telomeric C-ssDNA to form a duplex with a Tm value designated as Tmt;
   (2) synthesizing a template probe G, a middle part thereof being a repeated sequence $(TTAGGG)_{(n-1)}$, each end of the template probe G being a PCR primer sequence of a telomerase, wherein an enzyme cleavage site is located between the repeated sequence $(TTAGGG)_{(n-1)}$ and the PCR primer sequence at one end that is named as end A the template probe G has an ability to complementarily bind to the telomeric C-ssDNA to form a duplex with a Tm value designated as Tmc;
   (3) synthesizing an inhibitory probe S complementary to the enzyme cleavage site at the end A of the template probe G, the inhibitory probe S having an ability to complementarily bind to telomeric C-ssDNA to form a duplex with a Tm value designated as Tms, wherein the Tmc is 5° C. lower than Tmt and 20-25° C. higher than Tms;
   (4) forming a double-stranded DNA sequence cleavable by an enzyme from the template probe G and the inhibitory probe S, the double-stranded DNA sequence being designated as dsGS; and
   (5) carrying out a PCR reaction.

2. The method of claim 1, wherein the anchor probe T has a sequence of:

(SEQ ID NO: 1)
5'-TTAGGGTTAGGGTTAGGGTTAGGGTTAGGGTTAGGGTTAGGG-3', the template probe G has a sequence of:

(SEQ ID NO: 2)

5'-AAGAGCCGCGAGCGATCC*TTAGGGTTAGGGGTTAGGGTTAGGGTTAGGG**TTAGGGGATCC*GTCACCCTGGATGCTGTAGG-3', the inhibitory probe S has a sequence of:

(SEQ ID NO: 3)
5'-GTGAC*GGATCC*CTAACC-3', and the PCR primers are:

```
an upstream primer:
                                   (SEQ ID NO: 4)
5'-CCGTCACCCTGGATGCTGTAGG-3';
and a downstream primer:
                                   (SEQ ID NO: 5)
5'-AAGAGCCGCGAGCGATCCTT-3'.
```

3. The method of claim 1, wherein the method further comprises treating a sample with a lysis buffer with a composition of: 1 mmol/L of EDTA-Na, 1% of Triton X-100, 150 mmol/L of NaCl, 10% of glycerol, 0.1 mg/ml of fish sperm DNA, and 10 mmol/L of Tris-HCl with pH 7.5.

4. The method of claim 1, wherein the PCR reaction is carried out with a solution with a composition of: 50 mmol/L of KCl, 1.5 mmol/L of MgCl$_2$, 0.2 mmol/L of dNTP, 0.05% of Tween 20, 0.4× SYBR Green I, 1 U/50 μl of Taq enzyme, 4 U/50 μl BamHI, 0.2 umol/L of PCR primers, and 10 mmol/L of Tris-HCl with pH 9.0.

5. A kit for detecting alternative lengthening of telomere, which comprises: an anchor PCR tube comprising an anchor probe T fixed thereto, a template probe G, an inhibitory probe S, PCR primers, a PCR reaction buffer, a Taq enzyme, and a BamHI enzyme, wherein the anchor probe T has a sequence of:

(SEQ ID NO: 1)
5'-TTAGGGTTAGGGTTAGGGTTAGGGTTAGGGTTAGGGTTAGGG-3', the template probe G has a sequence of:

(SEQ ID NO: 2)

5'-AAGAGCCGCGAGCGATCC*TTAGGGTTAGGGGTTAGGGTTAGGGTTAGGG**TTAGGGGATCC*GTCACCCTGGATGCTGTAGG-3', the inhibitory probe S has a sequence of:

(SEQ ID NO: 3)
5'-GTGAC*GGATCC*CTAACC-3', wherein the highlighted italicized part of the sequence is a BamHI restriction site, and the PCR primers are:

```
an upstream primer:
                                   (SEQ ID NO: 4)
5'-CCGTCACCCTGGATGCTGTAGG-3';
and a downstream primer:
                                   (SEQ ID NO: 5)
5'-AAGAGCCGCGAGCGATCCTT-3'.
```

6. The kit of claim 5, wherein the kit further comprises a cell lysis buffer having a composition of: 1 mmol/L of EDTA-Na, 1% of Triton X-100, 150 mmol/L of NaCl, 10% of glycerol, 0.1 mg/ml of fish sperm DNA, and 10 mmol/L of Tris-HCl with pH 7.5 as a solvent.

* * * * *

SEQUENCE LISTING

```
<160> NUMBER OF SEQ ID NOS: 6

<210> SEQ ID NO 1
<211> LENGTH: 42
<212> TYPE: DNA
<213> ORGANISM: Artificial Sequence
<220> FEATURE:
<223> OTHER INFORMATION: anchor probe T

<400> SEQUENCE: 1
ttagggttag ggttagggtt agggttaggg ttagggttag gg                42

<210> SEQ ID NO 2
<211> LENGTH: 78
<212> TYPE: DNA
<213> ORGANISM: Artificial Sequence
<220> FEATURE:
<223> OTHER INFORMATION: template probe G
```

```
<400> SEQUENCE: 2
aagagccgcg agcgatcctt agggttaggg ttagggttag ggttagggtt agggatccgt    60
caccctggat gctgtagg                                                 78

<210> SEQ ID NO 3
<211> LENGTH: 17
<212> TYPE: DNA
<213> ORGANISM: Artificial Sequence
<220> FEATURE:
<223> OTHER INFORMATION: inhibitory probe S

<400> SEQUENCE: 3
gtgacggatc cctaacc                                                  17

<210> SEQ ID NO 4
<211> LENGTH: 22
<212> TYPE: DNA
<213> ORGANISM: Artificial Sequence
<220> FEATURE:
<223> OTHER INFORMATION: upstream primer

<400> SEQUENCE: 4
ccgtcaccct ggatgctgta gg                                            22

<210> SEQ ID NO 5
<211> LENGTH: 20
<212> TYPE: DNA
<213> ORGANISM: Artificial Sequence
<220> FEATURE:
<223> OTHER INFORMATION: downstream primer

<400> SEQUENCE: 5
aagagccgcg agcgatcctt                                               20

<210> SEQ ID NO 6
<211> LENGTH: 34
<212> TYPE: DNA
<213> ORGANISM: Artificial Sequence
<220> FEATURE:
<223> OTHER INFORMATION: TaqMan probe

<400> SEQUENCE: 6
cctaaccCTA accCTAaccc taaccctaac ccta                               34
```